United States Patent
Bonomi et al.

(10) Patent No.: US 12,042,304 B2
(45) Date of Patent: Jul. 23, 2024

(54) DETERMINING RELIABILITY OF VITAL SIGNS OF A MONITORED SUBJECT

(71) Applicant: KONINKLIJKE PHILIPS N.V., Eindhoven (NL)

(72) Inventors: Alberto Giovanni Bonomi, Eindhoven (NL); Laurentia Johanna Huijbregts, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 764 days.

(21) Appl. No.: 17/251,565

(22) PCT Filed: Jun. 6, 2019

(86) PCT No.: PCT/EP2019/064791
§ 371 (c)(1),
(2) Date: Dec. 11, 2020

(87) PCT Pub. No.: WO2019/238525
PCT Pub. Date: Dec. 19, 2019

(65) Prior Publication Data
US 2021/0251573 A1     Aug. 19, 2021

(30) Foreign Application Priority Data
Jun. 13, 2018   (EP) ..................... 18177435

(51) Int. Cl.
G16H 40/67     (2018.01)
A61B 5/00     (2006.01)
G16H 50/30     (2018.01)
A61B 5/11     (2006.01)

(52) U.S. Cl.
CPC ............ *A61B 5/7221* (2013.01); *A61B 5/746* (2013.01); *G16H 40/67* (2018.01); *G16H 50/30* (2018.01); *A61B 5/1116* (2013.01); *A61B 5/1118* (2013.01)

(58) Field of Classification Search
CPC ..... A61B 5/7221; A61B 5/746; A61B 5/1116; A61B 5/1118; G16H 40/67; G16H 50/30
See application file for complete search history.

(56) References Cited

U.S. PATENT DOCUMENTS

| | | | |
|---|---|---|---|
| 9,854,986 | B2 | 1/2018 | Quinlan et al. |
| 10,382,839 | B2 | 8/2019 | Aumer |
| 2005/0215868 | A1 | 9/2005 | Kenjou et al. |
| 2010/0298661 | A1 | 11/2010 | McCombie et al. |
| 2012/0029300 | A1 | 2/2012 | Paquet |

(Continued)

FOREIGN PATENT DOCUMENTS

| | | | |
|---|---|---|---|
| WO | 2015165785 | A1 | 11/2015 |
| WO | 2017108548 | A1 | 6/2017 |
| WO | 2018036988 | A1 | 3/2018 |

OTHER PUBLICATIONS

International Search Report and Written Opinion, International Application No. PCT/EP2019/064791, Mailed on Jul. 30, 2019.

*Primary Examiner* — Manuel A Rivera Vargas

(57) ABSTRACT

Presented are concepts for determining reliability of vital signs of a monitored subject. One such concept obtains activity data relating to detected activity or posture of the monitored subject. Based on the activity data and physiological data relating to one or more physical or physiological attributes of the monitored subject, a measure of reliability of vital signs of the monitored subject is determined.

13 Claims, 8 Drawing Sheets

(56) References Cited

U.S. PATENT DOCUMENTS

2015/0094545 A1* 4/2015 Russell ............... A61B 5/7282
                                                      600/301
2015/0099941 A1   4/2015  Tran
2015/0305689 A1  10/2015  Gourmelon et al.
2016/0015308 A1   1/2016  Kirenko et al.

* cited by examiner

DETERMINING RELIABILITY OF VITAL SIGNS OF A MONITORED SUBJECT

This application is the U.S. National Phase application under 35 U.S.C. § 371 of International Application No. PCT/EP2019/064791, filed on 6 Jun. 2019, which claims the benefit of European Application Serial No. 18177435.7, filed 13 Jun. 2018. These applications are hereby incorporated by reference herein.

FIELD OF THE INVENTION

This invention relates generally to monitoring a subject, such as a person or patient, and more particularly to determining reliability of vital signs of a monitored subject.

BACKGROUND OF THE INVENTION

Monitoring of a subject's health status or recuperation after injury, hospitalization and treatment is of primary concern in most branches of medicine, including geriatrics, rehabilitation and physical therapy, neurology and orthopaedics, nursing and elder care.

Warning systems are commonly used in low acuity settings of a hospital or medical care facility to provide an alert in the case of subject deterioration. Such warning systems are typically based on vital signs like heart rate, respiration rate, arterial oxygen saturation (SpO2), blood pressure, carbon dioxide and temperature. Such vital signs are normally monitored by intermittent, manual spot checks of the patient. These spot checks are performed at regular intervals, and their frequency depends on the severity of the patient and the number of staff.

Recent trends in patient monitoring systems are leading towards automatic and frequent (or even continuous) assessment of a subject's vital signs to improve the efficiency of early warning systems and decrease the workload of carers.

Monitoring devices including sensors that are continuously connected to the patient can perform unattended monitoring. Also, so that subjects are not restricted in their mobility (and may move or walk around, for example), wireless monitoring devices are typically preferred.

Such monitoring devices should submit reliable and actionable information, thereby avoiding excessive false and/or irrelevant alerts. However, physical activity, movement and/or posture changing of the monitored subject can cause metabolic and hemodynamic changes in the subject which can, in turn, result in alterations of vital signs of the monitored subject. Measurements taken while a subject is in different states may therefore result in inaccuracies in derived results, such as scores (e.g., early warning score (EWS)), and automatically detected patient deteriorations, as well as an increased number of irrelevant alerts. For example, a subject's heart rate may be elevated because the subject has just climbed some stairs, and this could lead to a clinically meaningless alert for high heart rate.

Accordingly, alterations in vital signs due to patient activity, movement and/or posture change may lead to false or incorrect alerts. It may therefore be desirable to develop concepts for reducing or preventing the generation of false alarms that may otherwise result from changes in vital signs due to physical activity, movement and/or posture changing of a monitored subject.

SUMMARY OF THE INVENTION

The invention aims to at least partly fulfil the aforementioned needs. To this end, the invention provides systems and methods as defined in the independent claims. The dependent claims provide advantageous embodiments.

There is provided a system for determining reliability of one or more vital signs of a monitored subject, the system comprising: a signal interface adapted to obtain activity data relating to detected activity or posture of the monitored subject; a data acquisition unit adapted to obtain physiological data relating to one or more physical or physiological attributes of the monitored subject; and a reliability unit adapted to determine a measure of reliability of one or more vital signs of the monitored subject based on the activity data and the physiological data.

Proposed is a concept for determining reliability of vital signs of a subject based on physical activity or posture of the subject. By using measurements of physical movement, activity, or posture of the subject, along with physiological characteristics of the subject, an impact of the movement, activity, or posture on one or more vital signs of the subject may be assessed or predicted. For example, by determining a measure of deviations (e.g. reliability measure) in vital signs of the subject caused by physical exertion, embodiments may enable the identification of when measurements of vital signs should be ignored or adjusted. This provides an indication of how representative current vital signs are for those vital signs when the subject would have been in a resting state for a long time.

Embodiments may therefore facilitate the identification of changes in vital signs that are meaningful and representative of underlying changes in a person's physical or mental capability, as distinct from changes caused by physical activity and/or posture changes of the monitored subject. This may help to reduce a number of false alarms (i.e. inaccurate or incorrect monitoring decisions) and provide more accurate monitoring. Further, embodiments may be used for evaluation purposes, for example to assess if a subject shows a significant change in one or more vital signs.

For example, proposed embodiments may be employed to determine (or predict) when vital signs are not significantly disturbed by the subject's physical activity. It may thus be identified when vital signs are considered reliable (e.g. when the monitored subject is in a rest state) and useful for monitoring the subject. In this way, an appreciation of how representative current vital signs are of a resting state of the subject is provided by embodiments.

Reliability of one or more vital signs may therefore be inferred using a single sensor (e.g. accelerometer) worn or carried by the subject. This may help to reduce associated cost and/or complexity of a monitoring system. For instance, embodiments may avoid the need for multiple sensors (and complex signal processing of their respective signals) and may instead simply employ a single value (e.g. movement or posture) sensing arrangement.

Embodiments may be based on a proposal to determine the reliability or usefulness of vital signs measurements of a subject based on a detected activity or posture of the subject. Further, predictions may be made as to when the vital signs will stop to be significantly disturbed by previous physical activity (e.g. when the subject will be considered to be back in a resting state), and thus identify when an alarm or warning system may be switched on again).

Embodiments may therefore be able to distinguish between changes in vital signs that represent an actual change in a person's physical health, and other changes that may be the result of physical activity and/or posture changes of the person.

Improved (e.g. more accurate) monitoring of a subject's health or well-being may therefore be facilitated by using information relating to the subject's physical activity or posture. Embodiments may also be employed to infer a trend from detected changes in activity or posture of the subject, thereby enabling the prediction of when measured vital signs will be reliable (e.g. when the subject will return to a resting state).

Proposed embodiments may therefore be of particular relevance to patient monitoring since, for example, it may assist in interpretation of a variation of vital sign of a patient over time. Proposed concepts may also facilitate accurate signalling improvement or deterioration in the health status of a monitored, yet mobile subject.

In some proposed embodiments, the measure of reliability may comprise at least one of: a value of a recovery time required for the monitored subject to return to a resting state; and a measure of a deviation of a vital sign of the monitored subject from a resting value or range for the monitored subject in the resting state. A measure of deviation may, for example, represent an absolute difference of the current value of a vital sign from a resting state value of the vital sign. The measure of reliability may thus be representative of a level of influence of (current and/or recent) activity on a vital sign, and the measure may even be quantified in levels without units Accordingly, proposed concepts may enable the evaluation of whether vital signs of a subject such as heart rate, respiration rate, blood pressure, etc. are reliable for use in early warning systems. In this way, embodiments may avoid false alarms that would otherwise be generated as a result of changes in vital signs caused by physical activity of a monitored subject.

In proposed embodiments, the reliability unit may be adapted to determine a resting state of the monitored subject based on the physiological data. This may provide the advantage that specific attributes of the subject can be used to more accurately determine an impact or influence that activity has on the subject's vital signs. It may also enable more accurate determination of when a monitored subject may be in a resting state, and thus when vital signs may be reliable and useful for monitoring purposes.

In some embodiments, the signal interface may be further adapted to obtain vital sign data relating to a detected value of a vital sign of the monitored subject. Further, the system may further comprise a prediction unit adapted to determine a predicted value of the vital sign of the monitored subject at rest based on the vital sign data and the measure of reliability of vital signs of the monitored subject. For example, by taking account of a current value of a vital sign and its reliability (e.g. deviation from a normal/expected value for the subject caused by physical activity or posture), it may be predicted or extrapolated when the subject may be considered to return to a resting state. This may, in turn, facilitate the prediction or identification as to when measure vital signs of the subject will be useful for monitoring purposes (and not excessively altered by the subject's activity or change in posture).

The reliability unit may be adapted: to compare a value of the physiological data with one or more threshold values to obtain a comparison result; to generate a characterising value based on the physiological data; and to determine a measure of reliability of vital signs of the monitored subject based on the comparison result and the characterising value. Simple mathematical functions may therefore be employed, enabling straight-forward and reduced-complexity implementation.

Proposed embodiments may further comprise a historical data interface adapted to obtain historical data relating to previous activity or posture of the monitored subject. The reliability unit may then be adapted to determine a measure of reliability of vital signs of the monitored subject further based on the historical data. Taking account of previously obtained information may improve accuracy of determinations or assessments, for example, via comparison and/or refinement of an obtained measure of reliability based on the historical data.

The reliability unit may be adapted to obtain a historical measure of reliability of vital signs of the monitored subject, the historical measure of reliability having been previously determined for previously detected activity or posture of the monitored subject. The reliability unit may then be adapted to determine a trend in the reliability of vital signs of the monitored subject based on the determined measure of reliability and the historical measure of reliability. This may provide the advantage the more accurate determinations/assessments may be made. It may also cater for unique characteristics or properties associated with the monitored subject.

Embodiments may further comprise a sensor adapted to detect a value of the activity or posture of the monitored subject and to generate a signal comprising activity data representative of the detected value. Preferably, the sensor may comprise at least one of: an accelerometer; a gyroscope; a movement sensor; a weight sensor; a pressure sensor; and a timing device. Further, the sensor may be adapted to be coupled to the person or the object.

For example, there exist many sensors that can be employed by a system according to an embodiment. Typical sensors include PIR (Passive Infra-Red; measure movement and presence), OC (open-close; measure state of doors, in particular front doors, windows, and cupboards, including refrigerators), and pressure sensors or mats (measure occupancy of user sitting in chair, lying in bed, standing on door mat in front of front door, being at toilet, etc.). Many others exist and are conceivable, such as sensors to signal light switch state, etc. A further range of sensors are those based on physical quantities, such as accelerometers, magnetometers, gyroscopes, and air pressure sensors. Accelerometers, for example, can also measure speed or velocity of movement of a person or an object moved by the person. Yet another range of sensors consists of microphones and cameras (including infra-red, or even UV and beyond, part of spectrum), to which also belong GPS and location-sensitive IR. Ultra-sound or RF-based sensors, including RFID tagging, provide additional input. Appliances having an own IP-address, known as the internet-of-things, provide further sensor input signals that can be taken by the smart-home system.

Although the sensor(s) may be mounted in a monitoring environment (e.g. the person's home), they may also be attached to user utilities (such as a keyring) or put in clothes, in a pocket or bag, or as insole or undergarment, etc. They may also be fabricated to be worn explicitly like a wrist watch or pendant. By way of further example, some embodiments may employ a sensor that is adapted to be coupled to the person or the object.

The activity data relating to detected activity or posture of the monitored subject may comprise a value of at least one of: a velocity of movement of the subject; a measure of force applied by the subject to an object; a distance travelled by a part of the subject; a rate of acceleration of part of the subject; a measure of posture of the subject.

Further, the sensors may communicate their output signals to an interface of an embodiment via a wired or wireless connection, or a combination thereof. Accordingly, in an embodiment, the sensor may be adapted to be coupled to the person or the object.

Embodiments may therefore be implemented in conjunction with pre-existing, pre-installed or otherwise separately-provisioned presence or activity sensors, and the output signals from such sensors may be received and processed in accordance with proposed concepts. Other embodiments may be provided with sensors (e.g. where appropriate sensors are not already available).

A sensor may also be adapted to undertake primary processing of the detected values, such a signal filtering, sampling, conditioning, etc., so as to reduce required transmission bandwidth and/or transmission duration for example. Alternatively, a sensor may send raw data.

The sensor arrangement/system may be positioned in a strategic position so that it detects the appropriate value without the person needing to intentionally or consciously activate/operate the sensor. In this way, a person may only need to undertake their normal activities. Such strategic positioning may ensure that a value of a property of the person or object can be automatically and accurately obtained, and this may not require the person to remember to undertake any special or additional activities in order for a value to be detected by the sensor. This may remove the risk of the person forgetting to activate a sensor (e.g. by pressing a button), for example.

Non-intrusive monitoring may therefore be realized with relatively simple sensors that provide data on specific properties/parameters of an object or properties of the person (such as movement, weight, speed, and/or distance travelled for example). Such sensors for measuring activity or posture of the subject may be simple, small and/or cheap.

Thus, monitoring systems of the invention may employ conventional sensors and/or existing sensor arrangements. Also, embodiments may employ sensors that are considered to be non-intrusive and more easily accepted by the monitored person. Yet, with the data provided by these sensors, the reliability or usefulness of variations in a subject's vital signs may be determined and provide information on the person being monitored.

Such sensors may be employed by, or in conjunction with, embodiments so as to increase the number and/or accuracy of monitored activity and/or posture. They may also be used to confirm or qualify readings taken by a primary sensor, so that spurious or unintentional measurements are avoided. For example, signals from a location sensor worn by the monitored person may be used to confirm if movement readings taken by a movement sensing system are indeed attributable to the monitored subject.

Embodiments may be further adapted to store data in a database adapted to store historical data relating to one or more previously obtained activity data and/or determined measures of reliability. Previously obtained data and/or determined values may therefore be stored, in a historical database for example, and then used in subsequent calculations. Furthermore, currently determined values may be used to re-calculate or refine a previously determined trend, prediction or estimation.

It will be appreciated that all or part of a proposed system may comprise one or more data processing units. For example, the system may be implemented using a single processor which is adapted to undertake data processing in order to determine reliability of vital signs of a monitored subject.

The system for determining reliability of vital signs of a monitored subject may be remotely located from the activity/posture sensor(s), and a signal representative of detected values may be communicated to the system unit via a communication link.

The system may comprise: a server device comprising the signal interface, data acquisition unit and reliability unit; and a client device comprising the sensor(s). Dedicated data processing means may therefore be employed for the purpose of determining reliability of vital signs of a monitored subject, thus reducing processing requirements or capabilities of other components or devices of the system.

The system may further comprise a client device, wherein the client device comprises the signal interface, data acquisition unit and reliability unit and a display system. In other words, a user (such as a care giver) may have an appropriately arranged client device (such as a laptop, tablet computer, mobile phone, PDA, etc.) which processes received activity data and physiological data in order to determine a reliability of vital signs of a monitored subject.

Thus, processing may be hosted at a different location from where the activity/posture sensing happens. For example, for reasons of power efficiency (e.g. to improve battery lifetime) it might be advantageous to execute only part of the processing at the sensor location, thereby reducing associated costs, processing power, transmission requirements, etc.

Thus, it will be understood that processing capabilities may therefore be distributed throughout the system in different ways according to predetermined constraints and/or availability of processing resources.

Embodiments may also enable some of the processing load to be distributed throughout the system. For example, pre-processing may be undertaken at an activity sensor system. Alternatively, or additionally, processing could be undertaken at a communication gateway. In some embodiments, processing may be undertaken at a remote gateway or sever, thus relinquishing processing requirements from an end-user or output device. Such distribution of processing and/or hardware may allow for improved maintenance abilities (e.g. by centralising complex or expensive hardware in a preferred location). It may also enable computational load and/or traffic to be designed or located within a networked system according to the processing capabilities available. A preferable approach may be to process sensor signals locally and transmit extracted data for full processing at a remote server.

The one or more physical or physiological attributes of the monitored subject may comprise at least one of: height; weight; age; gender; existing disease(s); anaerobic power; strength; somatotype; relative size; aerobic profile; agility; recovery ability; and level of fitness. Any suitable physical or physiological properties, attributes, traits or characteristics of a subject that may influence an amount by which activity or posture of the subject impacts his/her vital signs may therefore be accounted for. Embodiments may also take account of factors that may influence such attributes, such as prescribed medication, diet, supplementation, sleeping pattern, or injury for example.

Values of the physical or physiological attributes of a subject may be objective, and thus simply measured or determined/detected using appropriate techniques/methods, However, some physiological attributes (such as recovery ability; and level of fitness for example) may be estimated. Such physical or physiological attributes may be estimated by a user (e.g. the subject, carer, or family member) and provided as a user input and/or they may be learned/inferred from activity data in combination with vital signs measurements. A combination is also possible—for example, a recovery ability/level of fitness may first be estimated by a user provide by via a user input, then an embodiment may subsequently adapt these in response to the subject's vital signs resulting from activity. If not provided as a user input, default values for physical or physiological attributes may be used, and these may be calculated based on known physical or physiological attributes of the subject (e.g. height, weight, age, and/or gender). This may enable tailored or personalised assessment of a reliability of vital signs for a monitored subject. More accurate results may therefore be provided by proposed embodiments.

It is to be understood that reference to vital signs is considered to be different from reference to physical or physiological attributes, and also different from detected activity or posture. Such distinction may be explained on the premise that vital signs (often shortened to just vitals) are typically known as a group of the most important signs that indicate the status of a body's vital (life-sustaining) functions. Measurements of vital signs are taken to help assess the general physical health of a person, give clues to possible diseases, and show progress toward recovery. Normal or expected ranges for a subject's vital signs vary with physical or physiological attributes such as age; gender; existing disease(s); anaerobic power; strength; somatotype; relative size; aerobic profile; agility; recovery ability; and level of fitness. There are four primary vital signs: body temperature, blood pressure, pulse (heart rate), and breathing rate (respiratory rate), often notated as BT, BP, HR, and RR. However, depending on the clinical setting, the vital signs may include other measurements called the "fifth vital sign" or "sixth vital sign".

Detected activity may include any one of: a velocity (e.g. translational and/or rotational) or speed of movement of part of the subject; a measure (such as magnitude, speed/rate of change, average, etc.) of force (or derivatives thereof) applied by the subject to an object; a distance travelled by a body part of the subject; a rate of acceleration of a body part of the subject; and measure of posture of the subject. By detecting values of activity or posture of a subject, a change in the detected values over time may be identified and, from such changes, a measure of reliability of vital signs of the subject may be inferred and monitored.

The reliability unit may be further adapted to generate an output signal based on the determined measure of reliability of vital signs of the monitored subject. Embodiments may be adapted to provide an output signal to at least one of: the subject; a medical practitioner; and a caregiver. The output signal may thus be provided to a user or monitoring system for the purpose of indicating if measured vital signs should be ignored or overlooked for example.

Embodiments may further comprise a user input interface adapted to receive a user input for defining or modifying activity data and/or physiological data.

The reliability unit may be further adapted to generate a control signal for modifying a graphical element based on the determined measure of reliability of vital signs of the subject. Further, the system may further comprise a display system adapted to display the graphical element in accordance with the control signal generated by the reliability unit. In this way, a user (such as a care giver) may have an appropriately arranged display system that can receive and display information about the reliability of vital signs of the monitored subject, and that user may be remotely located from the subject. Embodiments may therefore enable a user to remotely monitor a subject (e.g. patient) using a portable display device, such as a laptop, tablet computer, mobile phone, PDA, etc.

According to another aspect of the invention, there is provided a system for monitoring vital signs of a subject, the system comprising: an input interface adapted to obtain vital signs data relating to one or more detected vital signs of the subject; a sensor arrangement adapted to detect a value of activity or posture of the monitored subject and to generate activity data representative of the detected value; a system for determining a reliability of vital signs of the monitored subject according to a proposed embodiment; and a processing unit adapted to process the vital signs data based on the determined reliability of vital signs of the monitored subject.

The processing undertaken by the processing unit may comprise at least one of: preventing an alarm from being activated; postponing collection of further vital signs data relating to detected vital signs of the subject; preventing the vital signs data relating to one or more detected vital signs of the subject from being provided to a warning system; and determining a value of a physical or physiological attribute of the subject based on the vital signs data and the determined reliability of one or more vital signs of the monitored subject. For the latter, the vital signs measurements are continued to be taken even during the periods where the reliability is low. In this way, obtained vital signs may be used to determine a physical or physiological attribute (e.g. level of fitness, recovery ability, etc.), or, in other words, to learn the response of the subject's vital signs to activity. Embodiments may therefore still make use of (e.g. learn from) measured vital signs even when it is determined that the vital signs aren't representative of a resting state of the subject (and should therefore be ignored for the purpose of providing an early warning for example).

According to another aspect of the invention, there is provided a method for determining reliability of vital signs of a monitored subject, the method comprising: obtaining activity data relating to detected activity or posture of the monitored subject; obtaining physiological data relating to one or more physical or physiological attributes of the monitored subject; and determining a measure of reliability of vital signs of the monitored subject based on the activity data and the physiological data.

According to yet another aspect of the invention, there is provided a method for monitoring vital signs of a subject, the method comprising: obtaining vital signs data relating to one or more detected vital signs of the subject; detecting a value of activity or posture of the monitored subject and to generate activity data representative of the detected value; determining reliability of vital signs of the monitored subject according to a proposed embodiment; and processing the vital signs data based on the determined reliability of vital signs of the monitored subject.

According to yet another aspect of the invention, there is provided computer program product for determining reliability of vital signs of a monitored subject, wherein the computer program product comprises a computer-readable storage medium having computer-readable program code embodied therewith, the computer-readable program code configured to perform all of the steps of an embodiment.

A computer system may be provided which comprises: a computer program product according to an embodiment; and one or more processors adapted to perform a method according to an embodiment by execution of the computer-readable program code of said computer program product.

In a further aspect the invention relates to a computer-readable non-transitory storage medium comprising instructions which, when executed by a processing device, execute the steps of the method of controlling a monitoring system display unit according to an embodiment.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying drawings, in which.

DETAILED DESCRIPTION OF THE EMBODIMENTS

Figure 1:
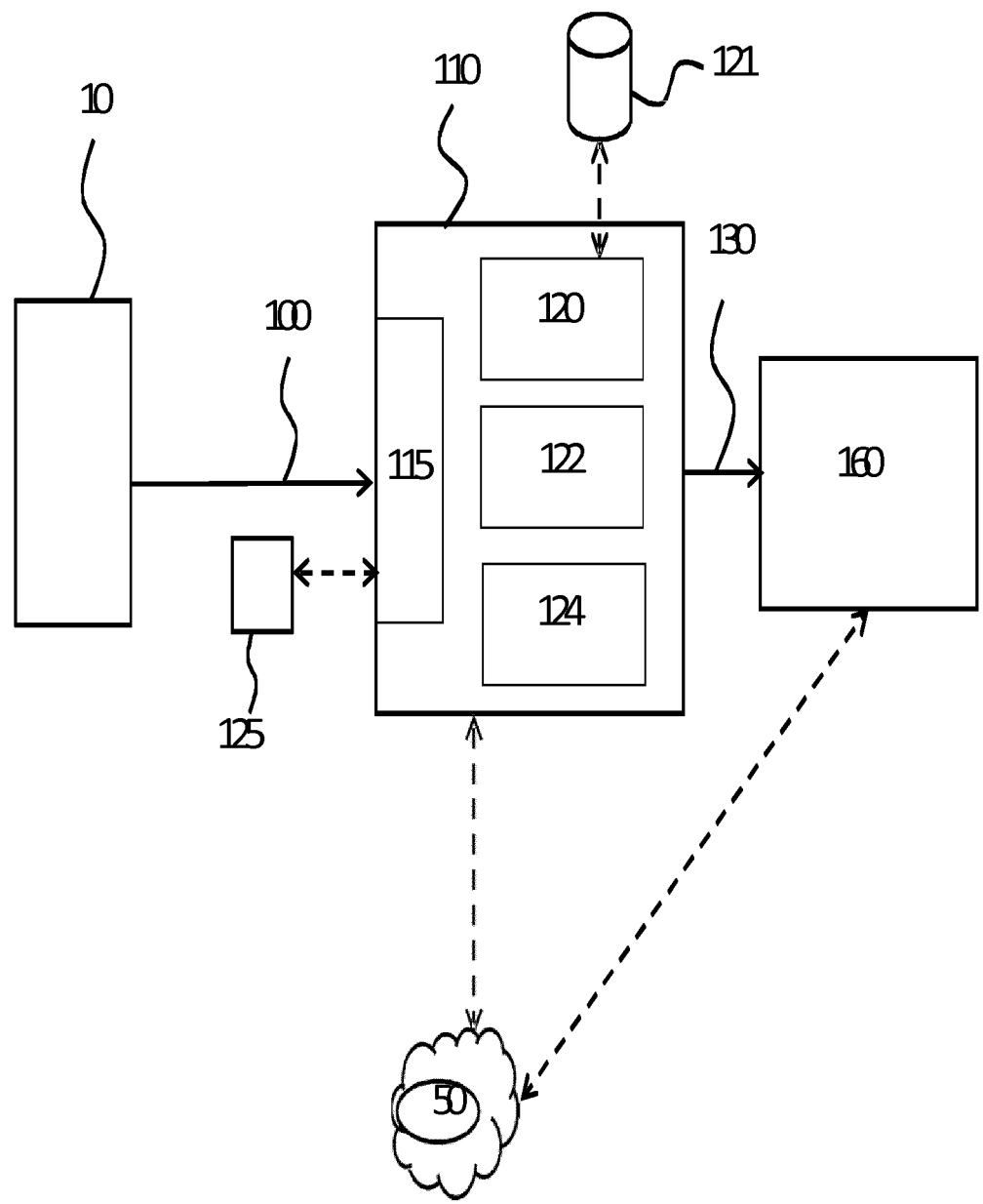
FIG. 1 is a simplified block diagram of a system for monitoring a subject according to an embodiment.

Proposed is a concept for determining reliability of vital signs in ambulatory subjects, which may be useful for improving health deterioration assessment and monitoring for example. Such subjects may, for instance, include a disabled person, an elderly person, an injured person, a medical patient, etc. Elderly persons can mean persons above 50 years, above 65 years, above 70, or above 80 years old, for example.

Illustrative embodiments may be utilized in many different types of monitoring environments, such as a hospital, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

Embodiments of the present invention are directed toward enabling unreliable vital signs of a subject to be identified and potentially dismissed/ignored. Such information may therefore be useful for improved monitoring accuracy or efficiency, e.g. by avoiding or reducing a number of false alarms.

Embodiments employ the concept of determining the reliability of vital signs based on a subject's physical activity or posture. Such activity or posture may be sensed using a wearable movement for example. Further, by considering one or more physical or physiological attributes of the subject, the influence of the subject's physical activity or posture on his/her vital signs may be assessed. Warning systems may then be activated/triggered only when the vital signs are considered to be reliable (e.g. representative of the subject at rest).

By determining a measure of reliability in vital signs, embodiments may enable the identification of a meaningful change in a vital sign of a subject that is significant and/or representative of an underlying changes in a person's physical health. This may help to reduce a number of false-positives (i.e. inaccurate or incorrect instances) and provide more accurate monitoring. Thus, embodiments may be useful for evaluation or monitoring purposes, for example to assess if a subject shows a significant improvement in a physical health.

Physical activity or posture may be detected or inferred from sensor output signals and there already exist systems and methods for such detection or inference. Accordingly, the proposed concepts may be used in conjunction with existing activity/posture detection or monitoring systems/methods. For example, Dries Vermeiren et al describe a system based on 2 tri-axial accelerometers to detect the Activities of Daily Living (ADLs) of a patient in a paper entitled "Detecting Human Motion: Introducing Step, Fall and ADL algorithms". Also, H Pirsiavas et al describe algorithms for detecting ADLs in first-person camera views in paper entitled "Detecting activities of daily living in first-person camera views" (CVPR, 2012). Further, in "Detection of type, duration, and intensity of physical activity using an accelerometer." (Medicine & Science in Sports & Exercise 41.9 (2009): 1770-1777), Bonomi, Alberto G., et al. describe a system that, based on a single tri-axial accelerometer positioned on the body trunk, can classify activity types such as walking, from actively standing or being sedentary, and define their duration and intensity in terms of metabolic expenditure. Because many such ADL detection or monitoring methods/systems are known and any one or more of these may be employed, detailed description of such methods/systems is omitted from this description.

FIG. 1 shows an embodiment of a system 1 according to the invention comprising a motion sensor 10 adapted to detect subject's movement of a subject.

Here, the motion sensor 10 is situated integrated into a portable device that is coupled to, carried or worn by the monitored subject so that it moves with movement of the subject. For example, the motion sensor 10 may comprise an accelerometer, magnetometer, and/or gyroscope.

In this way, a person need only undertake their normal activities when being monitored and may not even be aware that he/she is operating the motion sensor 10 and being monitored. Such configuration of the motion sensor 10 may enable movement of the subject to be detected without requiring the person to remember to undertake any special or additional activities in order for a movement or activity of the subject to be detected. For example, it can remove the need for a subject to perform a specific additional action (e.g. pressing a button) in order to activate the motion sensor 10.

The motion sensor 10 comprises a motion sensing arrangement that is adapted to determine a velocity of movement of the subject, a distance travelled by the subject, and a rate of acceleration of the subject (when the subject moves).

The motion sensor 10 is adapted to output sensor output signals 100 which are representative of the detected value(s) of the movement of the subject. Of course, many more sensors may be employed so as to provide signals indicative of detected values of properties of the activity or posture of the subject. For example, the magnitude of a pulling or pushing force applied by the subject to an object may be detected using one or more pressure sensors. Such additional signals may be useful for identifying which of the sensor output signals 100 are indicative of a property of the subject. They may also be used to confirm or qualify values detected by the motion sensor 10, so that spurious or unintentional measurements are avoided. For example, signals from a location sensor worn by the monitored subject may be used to confirm if values detected by the motion sensor 10 are indeed attributable to the monitored subject walking, for example.

The motion sensor 10 communicates its output signals 100 via a wired or wireless connection. By way of example, the wireless connection may comprise a short-to-medium-range communication link. For the avoidance of doubt, a short-to-medium-range communication link may be taken to mean a short-range or medium-range communication link having a range of up to around one hundred (100) meters. In short-range communication links designed for very short communication distances, signals typically travel from a few centimetres to several meters, whereas, in medium-range communication links designed for short to medium communication distances, signals typically travel up to one hundred (10)0 meters. Examples of short-range wireless communication links are ANT+, Bluetooth, Bluetooth low energy, IEEE 802.15.4, ISA100a, Infrared (IrDA), Near Field Communication (NFC), RFID, 6LoWPAN, UWB, Wireless HART, Wireless HD, Wireless USB, ZigBee. Examples of medium-range communication links include Wi-Fi, ISM Band, Z-Wave. Here, the output signals are not encrypted for communication via the wired or wireless connection in a secured manner. However, it will be appreciated that, in other embodiment, one or more encryption techniques and/or one or more secure communication links may be employed for the communication of signals in the system.

The system further comprises a system 110 for determining reliability of vital signs of a monitored subject. The system 110 has a signal interface 115 adapted to receive the sensor output signals 100. In this way, the signal interface 115 is adapted to receive activity data relating to detected activity or posture of the monitored subject. The activity data comprises information representative of a detected value of a property of the subject's activity or posture.

The system 110 also comprises a data acquisition unit 120 adapted to obtain physiological data relating to one or more physical or physiological attributes of the monitored subject. Here, the data acquisition unit 120 retrieves physiological data from a database 121 which is adapted to store values of physical or physiological attributes of the monitored subject, such as height, weight, age, gender, recovery ability, and level of fitness for example.

The obtained activity data and physiological data is provided to a reliability unit 122 of the system 110. The reliability unit 122 is adapted to process the activity data and physiological data to determine a measure of reliability of vital signs of the monitored subject. For this purpose, the reliability unit 122 of the system 110 may communicate with one or more data processing resources available in the internet or "cloud" 50. Such data processing resources may undertake part or all of the processing required to determine a measure of reliability.

In this example, the reliability unit 122 compares a value of the physiological data with one or more threshold values to obtain a comparison result, and generates a characterising value based on the physiological data. Based on the comparison result and the characterising value, the reliability unit 122 determines a measure of reliability of vital signs of the monitored subject. The measure of reliability comprises: a value of a recovery time required for the monitored subject to return to a resting state, and/or a measure of a deviation of a vital sign of the monitored subject from a resting value or range for the monitored subject in the resting state. Thus, for this purpose, the reliability unit 122 of this embodiment is also adapted to determine a resting state of the monitored subject based on the physiological data. For example, a resting state heart rate of the subject may be calculated using physiological data relating to the subject, such as height, weight, age, fitness level, etc.

The signal interface 115 of this embodiment is also adapted to obtain vital sign data relating to a detected value of a vital sign of the monitored subject. Here, such vital sign data is provided from a vital sign sensor 125, which is s a heart rate monitor in this example.

Obtained vital sign data is provided to a prediction unit 124 of the system 110. The prediction unit 124 is adapted to determine a predicted value of the vital sign (e.g. heart rate) of the monitored subject at rest based on the vital sign data and the measure of reliability determined by the reliability unit 122.

For example, if the determined measure of reliability comprise a value a deviation of heart rate of the monitored subject from a resting value or range for the monitored subject, this can be combined with a currently detected heart rate of the subject to predict a value of the heart rate devoid of changes caused by activity or posture. Put another way, the determined measure of reliability may be used to adjust a currently detected heart rate of the subject so as to cater for the activity or posture of the subject.

Again, for this purpose, the prediction unit 124 may communicate with one or more data processing resources available in the internet or "cloud" 50. Such data processing resources may undertake part or all of the processing required to determine a predicted value of the vital sign.

Thus, it will be appreciated that the embodiment may employ distributed processing principles.

The data processing system 110 is further adapted to generate an output signal 130 representative of a determined measure of reliability of vital signs of the monitored subject. In other words, after determining a measure of reliability of vital signs of the monitored subject based on obtained activity data and physiological data (either with or without communicating with data processing resources via the internet or "cloud"), an output signal 130 representative of or determined measure of reliability is generated.

The system further comprises a graphical user interface (GUI) 160 for providing information to one or more users. The output signal 130 is provided to the GUI 160 via wired or wireless connection. By way of example, the wireless connection may comprise a short-to-medium-range communication link. As indicated in FIG. 1, the output signal 130 is provided to the GUI 160 from the data processing unit 110. However, where the system, has made use of data processing resources via the internet or cloud 50), an output signal may be made available to the GUI 160 via the internet or cloud 50.

Based on the output signal 130, the GUI 160 is adapted to communicate information by displaying one or more graphical elements in a display area of the GUI 160. In this way, the system may communicate information about a measure of reliability of vital signs that may be useful for indicating if changes in vital signs are meaningful and representative of underlying changes in a person's physical or mental capability. For example, the GUI 160 may be used to display graphical elements to a medical practitioner, a caregiver, a family member or close relative. Alternatively, or in addition, the GUI 160 may be adapted to display graphical elements to the monitored person.

From the above description of the embodiments of FIG. 1, it will be understood that there is proposed a system for identifying whether changes in vital signs that are meaningful and representative of underlying changes in a person's physical capability (or otherwise simply caused by activity or posture). The system can be considered to comprise three main sub-systems/functions: (i) The first is a source of activity data—this may, for example, comprise a wearable sensor that can detect one or more properties of events (such as walking bouts or chair rises for example); (ii) The second implements a function for acquiring physiological data relating to one or more physical or physiological attributes of the monitored subject; and (iii) The third implements an algorithm determines a measure of reliability of vital signs of the monitored subject by analysing the activity data and the physiological data.

Although not detailed above for the embodiment of FIG. 1, in other embodiments, the reliability unit may be adapted to obtain a historical measure of reliability of vital signs of the monitored subject (e.g. from a database that is adapted to store previously determined measures of reliability for previously detected activity or posture of the monitored subject). The reliability unit may then further determine a trend in the reliability of vital signs of the monitored subject based on the determined measure of reliability and the historical measure of reliability.

From the above description, it will be appreciated that there is proposed a concept for evaluating whether the vital signs of a monitored subject (such as heart rate, respiration rate, blood pressure, etc.) are reliable for use in monitoring the subject (e.g. for early warning systems). This may address the issue of false alarms generated in response to changes in vital signs caused by physical activity of the subject. Proposed embodiments may therefore enable hospitals to evaluate patient deterioration more accurately and/or reliably.

A method according to an embodiment may be summarised as follows:

(i) Determine a measure of physical activity exerted by the monitored subject—e.g. determine the intensity, duration and/or type of the activity that the subject is undertaking;

(ii) Determine the activity history—e.g. calculate an index that represents the cumulative effect of the physical activity on the subject's vital signs over time. Such motion history index is updated according to the current activity type and/or intensity of the subject and according to the elapsed time from the previous activity (or set of activities);

(iii) Personalise model parameters—e.g. personalise a model of how activity impacts vital signs by changing or updating the value of model parameters according to physiological characteristics of the subject. This tailors the model to the subject;

(iv) Determine reliability of vital signs—e.g. determine whether the subject's measurements collected in a certain period are representative of a resting condition by evaluating whether the motion history index is below a certain threshold, which indicates that the previous activities or postural changes are no longer affecting the vitals of the subject patient;

(v) Extrapolate values of vital signs at rest:—an additional feature of proposed embodiment may estimate, by interpolation of a trend in vital signs, an expected value of a vital sign at rest. This may enable information on the subject's status to become available more quickly (e.g. even before the motion history has reached a required reliability level and the vitals are back to resting state).

Figure 2:
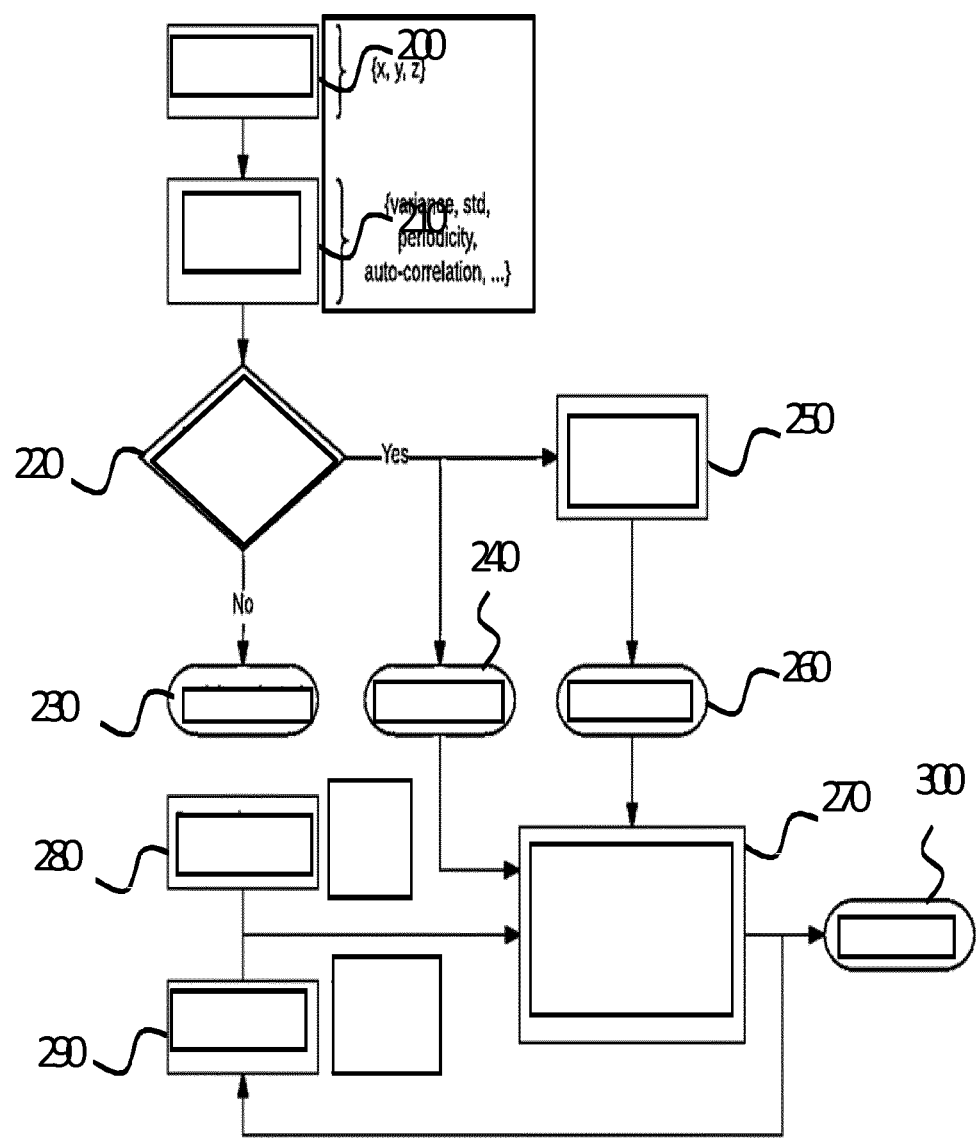
FIG. 2 is a flow diagram of an activity history calculation method that may be employed by an embodiment.

Referring now to FIG. 2, there is depicted a flow diagram of an activity history calculation method that may be employed by an embodiment. The method employs accelerometer data and estimates of activity intensity and type.

Firstly, in step 200, raw acceleration data is obtained from an accelerometer system attached to (or carried by) a monitored subject.

The acceleration data is then processed in step 210. The processing of step 210 includes calculating features of the acceleration data, such as the amplitude, variance, and frequency content.

The acceleration features are then compared against predetermined thresholds in step 220. Comparison against the thresholds is for determining whether the acceleration features are representative of activity.

If, in step 220, it is determined that the acceleration features do not exceed the threshold value(s), the method proceeds to step 230 wherein a result representative of the no activity being detected (e.g. "activity rejected") is output.

If, in step 220, it is determined that the acceleration features do exceed the threshold value(s), the method proceeds to steps 240 and 250. In step 240, a result identifying that activity has been detected (e.g. "activity detected") is output. In step 250, an intensity of the activity is determined, and the determined intensity is provided as a result representing the activity intensity (e.g. "motion level") in step 260. As an example, activity intensity can be represented by a value ranging from 1 to 5 based on an acceleration signal variance.

The outputs of steps 240 and 260 are provided to step 270. Also provided to step 270 is a determination of personal recovery time for the subject from step 280, along with a measure of activity history obtained from step 290.

The activity history is configured to be an index for the representability of the measured vital signs for the resting condition of the patient. This index is determined using information on physical load such as duration and intensity of the detected movement in a certain time interval (e.g. 5 minutes). The activity history index is constantly updated over time based upon: (i) the activity history value at a previous epoch, (ii) the current physical load of the subject, and (iii) a mean lifetime temporal constant which defines how quickly the vital signs will converge to a representative resting state.

The personal recovery time (hereinafter referred to as the mean lifetime temporal constant) can be personalized to a subject in a calibration phase. The mean lifetime temporal constant ($\tau$–tau) is required to update the activity history index when the subject is at rest and recovering after physical activity or posture change.

In step 270, an activity history index is calculated using the provided inputs (namely, the indication of detected activity from step 240, the activity intensity from step 260, the personal recovery time for the subject from step 280, and the measure of activity history obtained from step 290). The calculated activity history index is provided as an output 300 and also used to update the measure of activity history in step 290.

By way of example, the activity history index can be mathematically calculated according to the following equation:

$$Mh(t)=Mh(t-1)e\_dt/\tau,$$

where Mh indicates the activity history (e.g. motion history) at time t, dt is the time elapsed between time t−1 and t, and τ (tau) represents the temporal constant of the exponential decay and depends on the physical or physiological attributes of the subject.

Activity history can be expressed in units equivalent to those used to define the activity intensity. An example of how the activity history index (Mh) can be computed starting from a definition of activity level (AL) for the activity carried out by a subject is expressed in (Python™) code below (with explanatory comments being identified using the #(hash) symbol).

Import numpy
set variables of time: mean lifetime decay and elapsed time between motion level values deltaT=5#sec tau=15*(60/deltaT)

assign a time vector of activity level values to the variable AL, AL defined as integer values in range {1, 5}
AL=activity level.values
initialize the activity history index Mh vector to zero
Mh=numpy.zeros(len(AL))
for each value of AL determine and update the Mh
for i, val in enumerate(AL):
    #initialize Mh to the first value of AL
    if i==0:

$Mh[i]=val$ else:
    # if the current motion level is greater than the lowest possible value
    if (val>1):
    #if the previous Mh index was the lowest possible if($Mh[i-1]-1$):

update Mh according to AL $Mh[i]=val$ if the previous Mh index was greater than current AL value elif($Mh[i-1]>val$):

maintain Mh unchanged from the previous value $Mh[i]=Mh[i-1]$ else:
update Mh according to AL $Mh[i]=val$ if the current activity level is equal to the lowest possible value elif $val==1$:

if the previous Mh index iss greater than lowest possible value if $Mh[i-1]>1$:

update Mh according to previous Mh and mean lifetime constant of the exponential decay model $Mh[i]=numpy.max([1,Mh[i-1]*numpy.exp(-deltaT/tau)])$ update Mh according to the current AL value
    else:

$Mh[i]=val$

Figure 3A:
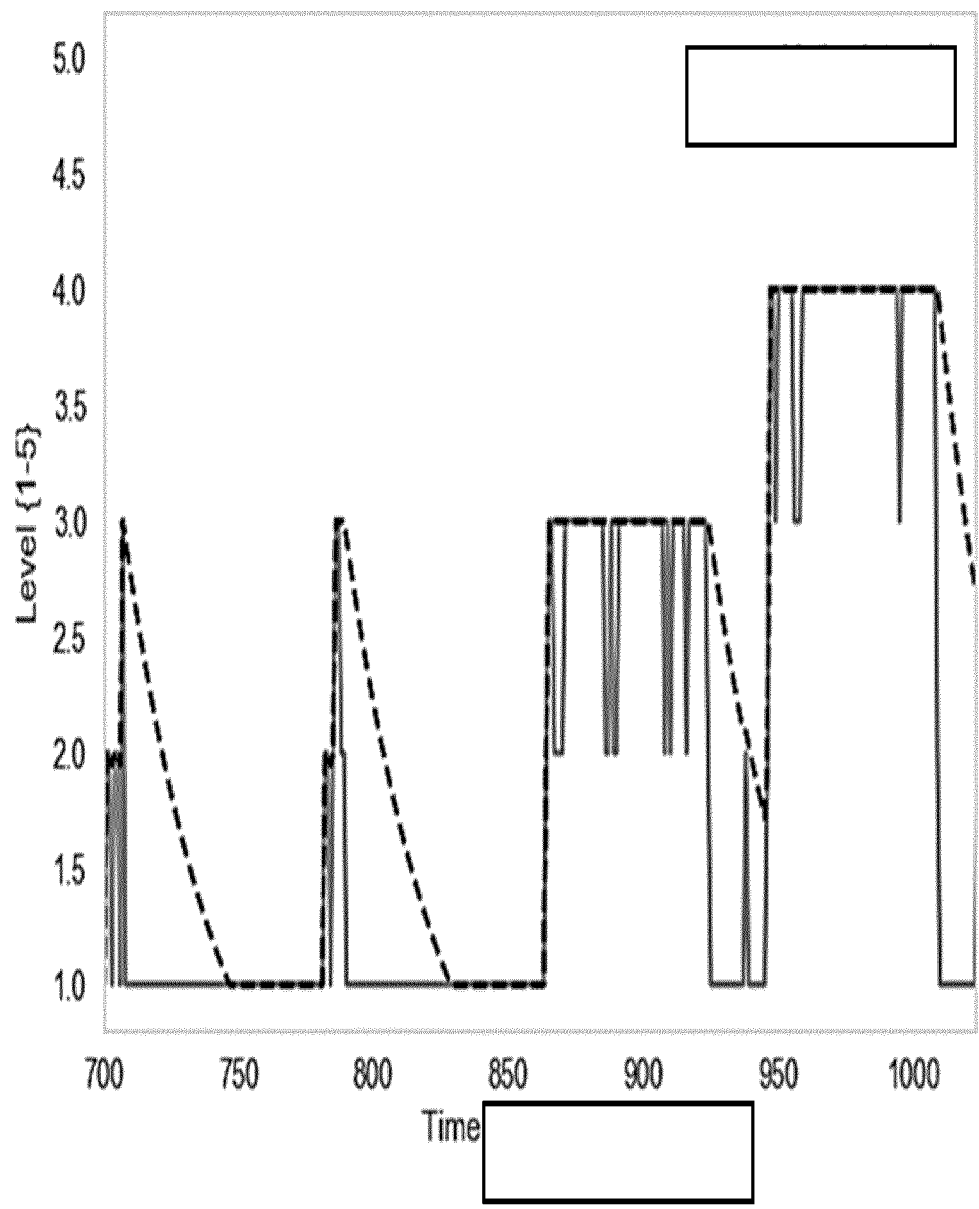
FIGS. 3A-3B are graphs illustrating the effect of different values of temporal constant of the exponential decay, wherein variation in activity intensity of a subject over time is plotted as a solid line, and the activity history index (Mh) for the subject is plotted as a dashed line.
Figure 3B:
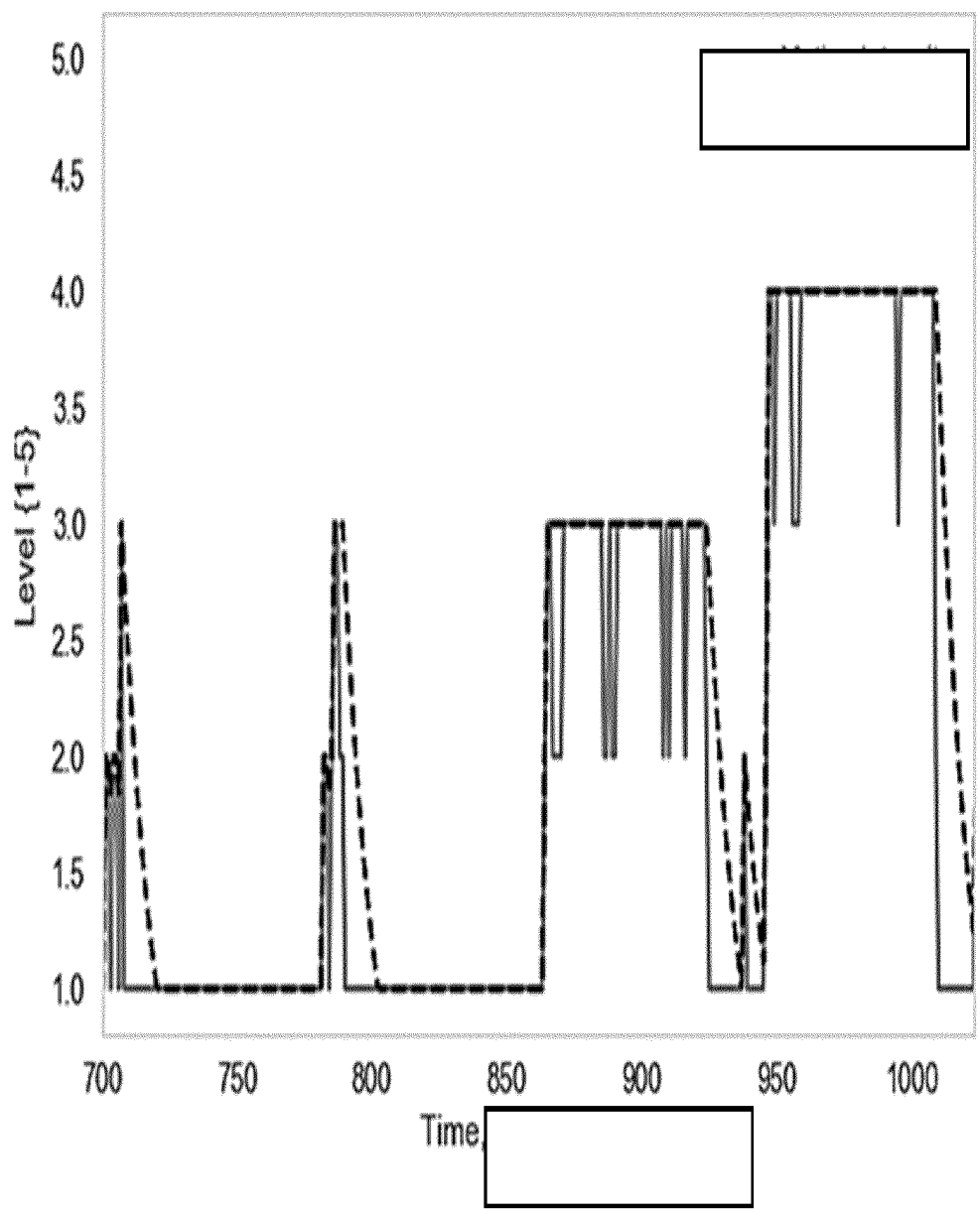

The resulting calculation is illustrated in FIGS. 3A and 3B for different values of temporal constant of the exponential decay. More specifically, the variation in activity intensity of a subject over time is plotted as a solid line, and the activity history index (Mh) for the subject is plotted as a dashed line. Here, the subject is changing posture two times and subsequently walking at two different speed for 5 minutes each time.

FIG. 3A displays a condition in which the activity history decays slower (thus, tau is larger) than in FIG. 3B. As a consequence, the vital signs associated with FIG. 3A will not be suitable for evaluation by the early warning score of the hospital during longer time periods.

Further, the algorithm designed to determine the changes in the activity history index can be tailored to the condition of a specific subject.

An embodiment can be adapted to measure vital signs of the subject in a calibration period. During such calibration, the temporal trend of the vital signs (e.g. heart rate or respiration rate) in response to physical activity or posture change can be registered and used to determine the mean lifetime temporal decay of the exponential model linking the activity history index to the time after which the vital signs have returned to the resting condition.

An alternative way to calculate the motion history is presented by the algorithm below based on an IRR filter of the motion intensity to determine the motion history.
Import numpy
set variables of the filtering algorithm determining motion history
gamma=0.05
assign a time vector of activity level values to the variable AL, AL defined as integer values in range {1, 5}
AL=activity_level.values
initialize the activity history index vector to zero
Mh=numpy.zeros(len(AL))
for each value of AL determine and update the Mh
for i, val in enumerate(AL):
    #initialize Mh to the first value of AL
    if i==0:

$Mh[i]=0$ else:

$Mh[i]=(1-gamma)*Mh[i-1]+gamma*val$

The approach above would cause the activity history index to resemble the temporal trends of vital signs more closely. The main difference with the earlier implementation is that the time to reach a reliability threshold is dependent on the activity intensity and duration. The longer the activity (of a certain intensity) the longer the time needed for the activity history index to reach a sufficiently low level as needed to consider the vital signs representative of the subject at rest.

Figure 4A:
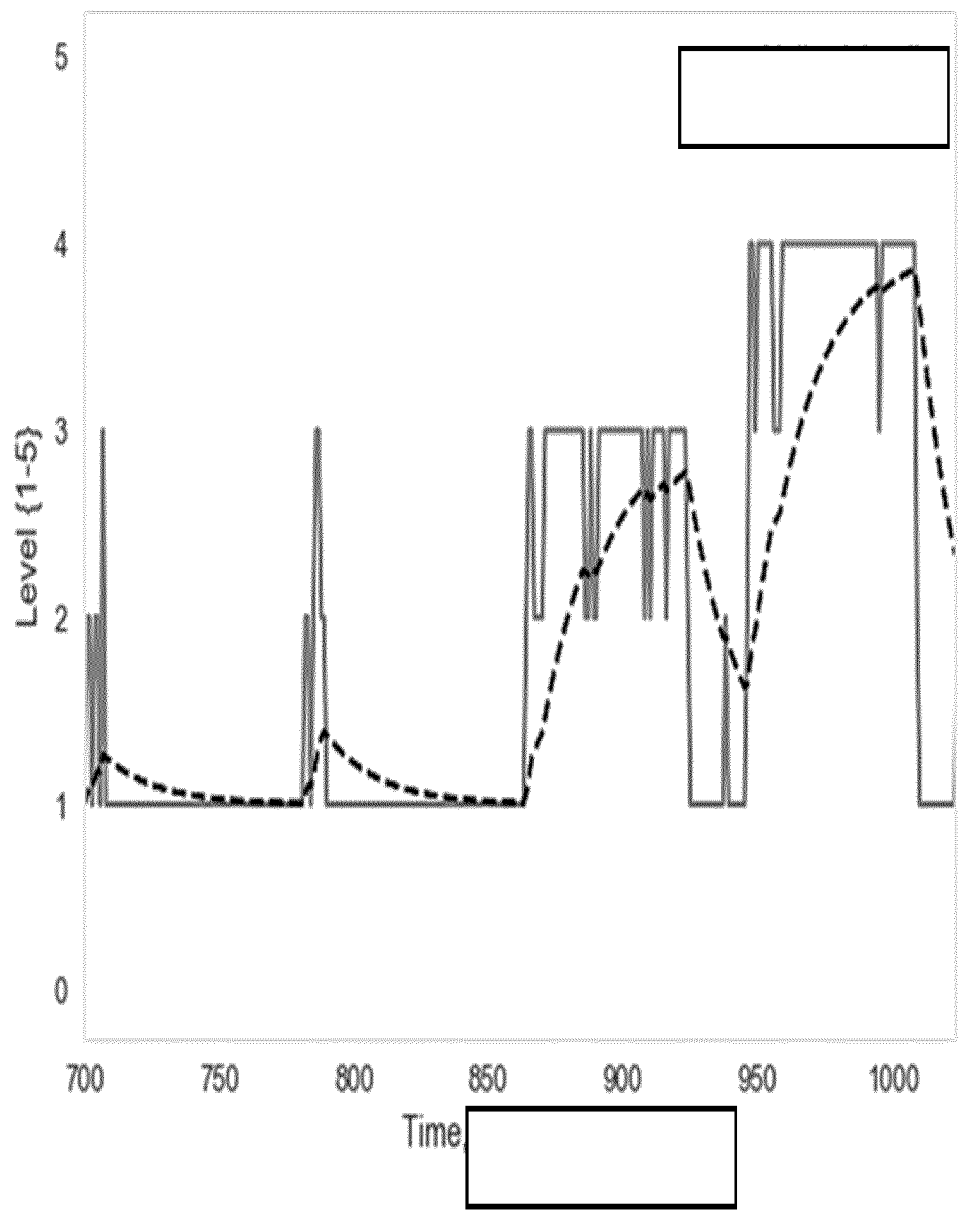
FIGS. 4A-4B are graphs illustrating the effect of such simple algorithm of subject data assuming different personal trends in vital signs as described by the coefficient gamma of the model, wherein the variation in activity intensity of a subject over time is plotted as a solid line, and the activity history index (Mh) for the subject is plotted as a dashed line.
Figure 4B:
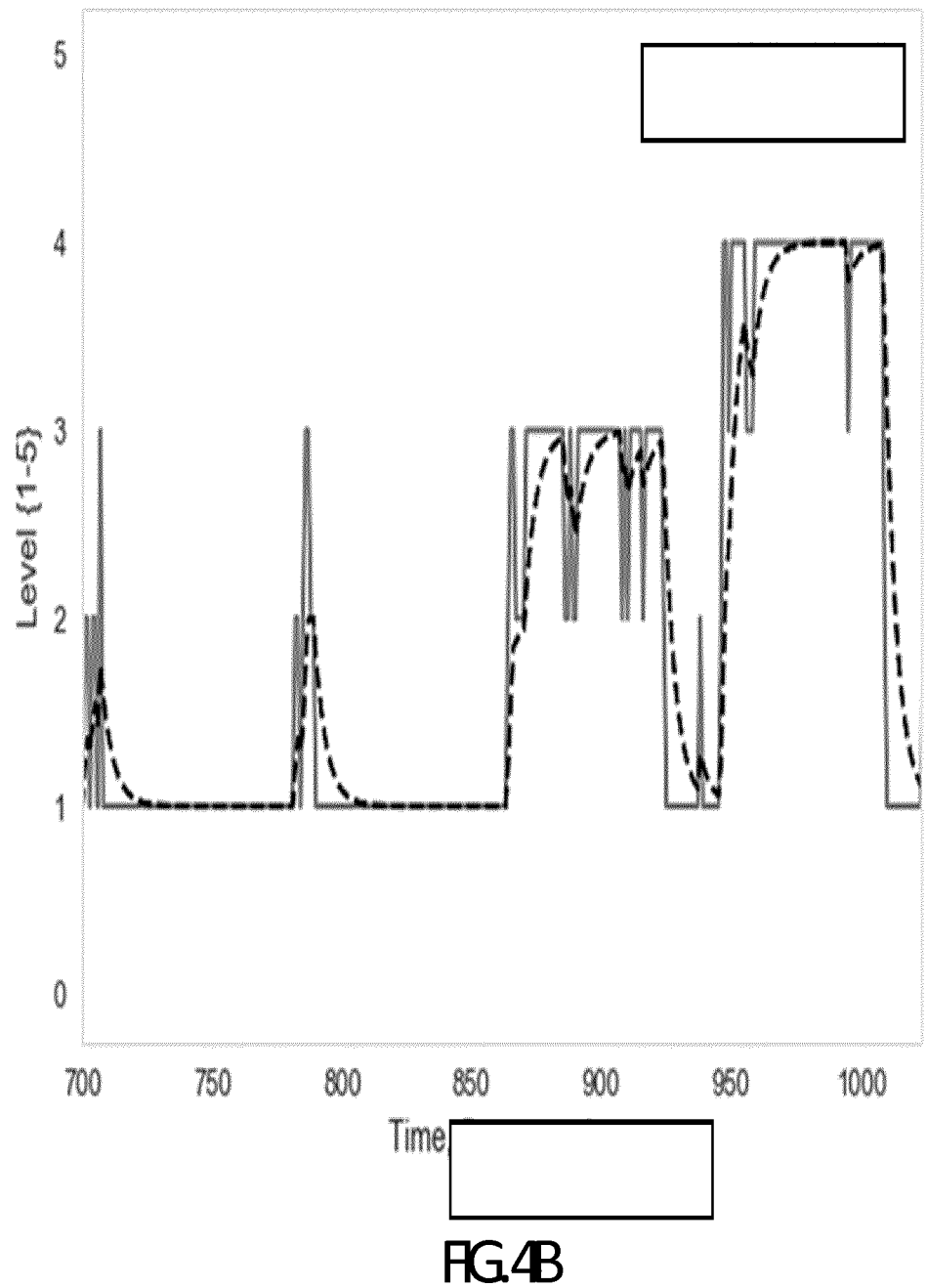

FIGS. 4A and 4B show the effect of such simple algorithm of subject data assuming different personal trends in vital signs as described by the coefficient gamma of the model. In FIGS. 4A and 4B, the variation in activity intensity of a subject over time is plotted as a solid line, and the activity history index (Mh) for the subject is plotted as a dashed line.

FIG. 4A displays a condition in which the activity history decays slower (thus, tau is larger) than the condition in FIG. 4B. As, as the vital signs associated with FIG. 4A will not be suitable for evaluation by the early warning score of the hospital during longer time periods.

In an alternative embodiment, personalized parameters (e.g. tau or gamma) of the activity history model could also be used to assess the ability of the subject to recover from physical load. This could help detecting deteriorating conditions in subjects and could be used to raise alarms beyond the outcome of the early warning score. For example, if tau becomes substantially larger than it was before, an alarm may be raised to warn for deterioration. On the other hand, a substantial decrease in tau may hint to the subject getting in a better condition and could therefore be used to give a notification to the caregiver that the subject might be ready for discharge from the hospital or nursing home.

Additionally, any large deviation between expected and observed decrease in vital signs after physical activity may also be used as a sign of deterioration or discharge readiness of the subject.

Tau and gamma may depend on the vital sign under study. For example, after activity, respiration rate usually gets back to its resting value earlier than heart rate does. Tau is therefore usually smaller for respiration rate than it is for heart rate. If the system of the invention is used for more than one type of vital sign, it might thus work with different values of tau and gamma for each vital sign.

Figure 5:
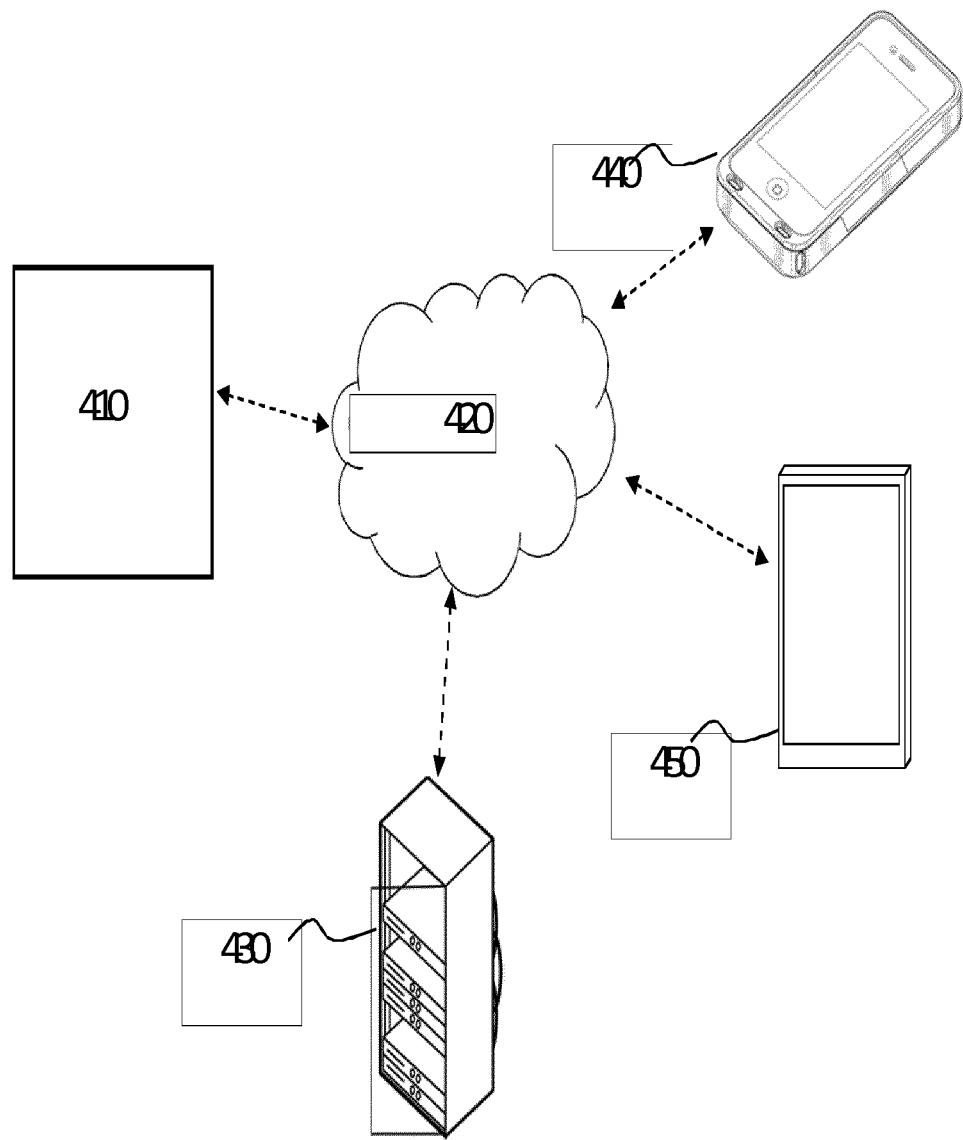
FIG. 5 is a simplified block diagram of a system for monitoring a subject according to another embodiment.

Referring now to FIG. 5, there is depicted another embodiment of a system according to the invention comprising an accelerometer arrangement 410 adapted to detect movement of the person. Here, the accelerometer arrangement 410 comprises a high-resolution tri-axis accelerometer arrangement 410 adapted to be integrated into a necklace or pendant that is worn by the monitored subject. The accelerometer arrangement 410 is adapted to output one or more signals which are representative of the detected value(s) of a subject's movement.

Although this embodiment has been described as employing a portable and wearable sensor arrangement, it will be understood that, in alternative embodiments, the movement of the subject may be detected using one or more sensors strategically positioned within a monitoring environment. For example, a movement detection system may be positioned at the entrance or doorway to a room so as to measure a subject's speed upon entering and leaving the room. Further, where multiple locations may be provided (e.g. on first and second floors, etc.), multiple movement sensing systems may be employed and the measurements combined.

The sensor 10 that measures the activity/posture might, or might not be, incorporated in the same device as the vital sign sensor 125. Activity/posture sensor 10 might even be the same sensor as vital signs sensor 125. For example, an accelerometer placed on the thorax, might both be used to measure activity/posture and to measure respiration rate. Another example is a camera that measures both activity and heart rate and/or respiration rate. On the other hand, the activity/posture sensor 10 might be completely separated from vital sign sensor 125, for example when the activity is measured with a device in the subjects pocket, while the vital sign comes from an SpO2 sensor on the subject's finger.

The accelerometer arrangement 410 communicates the output signals via the internet 420 (using a wired or wireless connection for example) to a remotely located data processing system for determining reliability of vital signs 430 (such as server).

The data processing system 430 is adapted to receive the one or more output signals from the accelerometer arrangement 410 (e.g. as activity data). The system is also adapted to obtain physiological data relating to one or more physical or physiological attributes of the monitored subject (e.g. from a local or remote database and/or via a user input interface).

The data processing system 430 processes the activity data and physiological data in accordance with a method according to a proposed embodiment to determine a measure of reliability of vital signs of the monitored subject. More specifically, the method compares a value of the physiological data with one or more threshold values to obtain a comparison result, generates a characterising value based on the physiological data, and then determines a measure of reliability of vital signs of the monitored subject based on the comparison result and the characterising value.

The data processing system 430 is further adapted to generate output signals representative of a determined measure of reliability of vital signs of the monitored subject. Thus, the data processing 430 provides a centrally accessible processing resource that can receive information from the accelerometer arrangement 410 and run one or more algorithms to transform the received information into a description of a measure of reliability of vital signs of the monitored subject. Information relating to the determined measure of reliability can be stored by the data processing system (for example, in a database) and provided to other components of the system. Such provision of information about a detected or inferred measure of reliability of vital signs of the monitored subject may be undertaken in response to a receiving a request (via the internet 420 for example) and/or may be undertaken without request (i.e. 'pushed').

For the purpose of receiving information about a detected or inferred measure of reliability of vital signs of the monitored subject from the data processing system, and thus to enable the subject's vital signs to be monitored accurately and/or in context, the system further comprises first 440 and second 450 mobile computing devices.

Here, the first mobile computing device 440 is a mobile telephone device (such as a smartphone) with a display for displaying graphical elements representative of a person's physical or mental well-being. The second mobile computing device 450 is a mobile computer such as a Laptop or Tablet computer with a display for displaying graphical elements representative of a person's mobility.

The data processing system 430 is adapted to communicate output signals to the first 440 and second 450 mobile computing devices via the internet 420 (using a wired or wireless connection for example). As mentioned above, this may be undertaken in response to receiving a request from the first 440 or second 450 mobile computing devices.

Based on the received output signals, the first 440 and second 450 mobile computing devices are adapted to display one or more graphical elements in a display area provided by their respective display. For this purpose, the first 440 and second 450 mobile computing devices each comprise a software application for processing, decrypting and/or interpreting received output signals in order to determine how to display graphical elements. Thus, the first 440 and second 450 mobile computing devices each comprise a processing arrangement adapted to one or more values representative of the subject's measure of reliability of vital signs, and to generate a display control signal for modifying at least one of the size, shape, position, orientation, pulsation or colour of the graphical element based on the one or more values representative of measure of reliability of vital signs.

The system can therefore communicate information about an inferred or detected measure of reliability of vital signs of a monitored subject to users of the first 440 and second 450 mobile computing devices. For example, each of the first 440 and second 450 mobile computing devices may be used to display graphical elements to a medical practitioner, a caregiver, a family member or close relative.

Implementations of the system of FIG. 4 may vary between: (i) a situation where the data processing system 430 communicates display-ready data, which may for example comprise display data including graphical elements (e.g. in JPEG or other image formats) that are simply displayed to a user of a mobile computing device using conventional image or webpage display (which can be web based browser etc.); to (ii) a situation where the data processing system 430 communicates raw data set information that the receiving mobile computing device then processes to determine a measure of reliability of vital signs, and then displays graphical elements based on the determined change (for example, using local software running on the mobile computing device). Of course, in other implementations, the processing may be shared between the data processing system 430 and a receiving mobile computing device such that part of the data generated at data processing system 430 is sent to the mobile computing device for further processing by local dedicated software of the mobile computing device. Embodiments may therefore employ server-side processing, client-side processing, or any combination thereof.

Further, where the data processing system 430 does not 'push' information (e.g. output signals), but rather communicates information in response to receiving a request, the user of a device making such a request may be required to confirm or authenticate their identity and/or security credentials in order for the information to be communicated.

It is also noted that, although it has been described above that embodiments need not employ additional/supplementary sensors, some embodiments may further comprise a sensor adapted to detect a value of a property of at least one of: the environment, control/operation of an object, and the monitored subject. Such a supplementary sensor arrangement may help to improve the accuracy of activity determination for example. Supplementary sensor readings may, for instance, qualify or refine data analysis undertaken. For instance, the subject may wear or carry an identification tag or location tracker which can enable embodiments to distinguish and disregard the presence of other people or animals detected by the presence sensors or movement sensors. By way of further example, signals from a location sensor worn by the monitored subject may be used to confirm if presence detections are indeed attributable to the monitored subject or some other person.

There exist many sensors that can be employed by embodiments. Typical sensors include PIR (pyroelectric infrared sensor; detect movement and presence) or pressure sensors. Many others exist and are conceivable, such as sensors comprising microphones and cameras (including infra-red (IR), or even UV and beyond, part of spectrum).

The sensors may also be adapted to undertake primary processing of the detected values, such a signal filtering, sampling, conditioning, etc., so as to reduce a required transmission bandwidth and/or transmission duration for example.

Non-intrusive monitoring may therefore be realized with relatively simple sensors that provide data on specific properties of the person (such as movement, for example). Also, the movement of the subject may be detected with sensors that are cheap and widely employed. For instance, movement sensors may be used to switch on lighting and people are therefore typically familiar with their usage. Thus, embodiments may employ sensors that are considered to be non-intrusive and more easily accepted by the monitored person. Yet, with the data provided by these sensors, a subject's activity may be accurately determined and provide more information on the subject being monitored. Thus, some embodiments of the invention may employ conventional sensors and/or existing sensor arrangements. Also, embodiments may employ sensors that are considered to be non-intrusive and more easily accepted by the monitored person.

Figure 6:
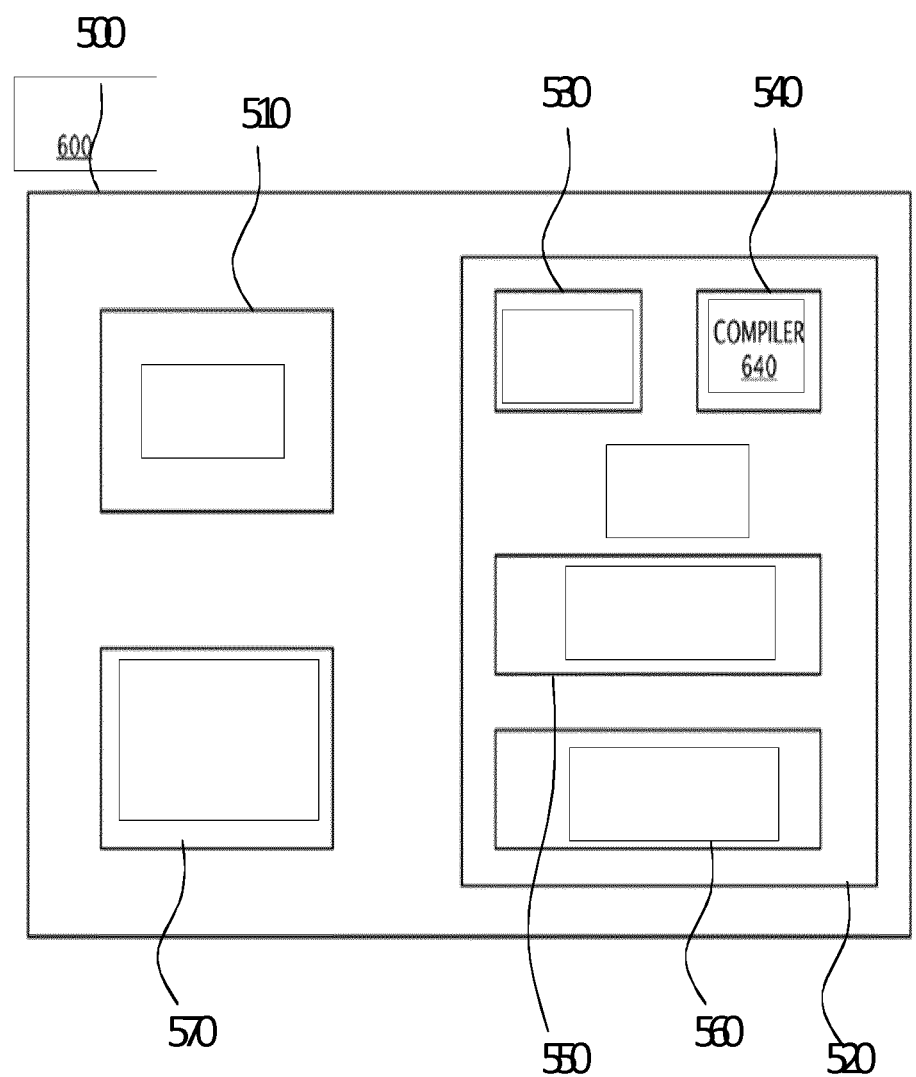
FIG. 6 is a simplified block diagram of a computer within which one or more parts of an embodiment may be employed.

FIG. 6 illustrates an example of a computer 500 within which one or more parts of an embodiment may be employed. Various operations discussed above may utilize the capabilities of the computer 500. For example, one or more parts of a monitoring system adapted to monitor a person may be incorporated in any element, module, application, and/or component discussed herein.

The computer 500 includes, but is not limited to, PCs, workstations, laptops, PDAs, palm devices, servers, storages, and the like. Generally, in terms of hardware architecture, the computer 500 may include one or more processors 510, memory 520, and one or more I/O devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a digital signal processor (DSP), or an auxiliary processor among several processors associated with the computer 500, and the processor 510 may be a semiconductor based microprocessor (in the form of a microchip) or a microprocessor.

The memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the memory 520 may include one or more separate programs, each of which comprises an ordered listing of executable instructions for implementing logical functions. The software in the memory 520 includes a suitable operating system (O/S) 550, compiler 540, source code 530, and one or more applications 560 in accordance with exemplary embodiments. As illustrated, the application 560 comprises numerous functional components for implementing the features and operations of the exemplary embodiments. The application 560 of the computer 500 may represent various applications, computational units, logic, functional units, processes, operations, virtual entities, and/ or modules in accordance with exemplary embodiments, but the application 560 is not meant to be a limitation.

The operating system 550 controls the execution of other computer programs, and provides scheduling, input-output control, file and data management, memory management, and communication control and related services. It is contemplated by the inventors that the application 560 for implementing exemplary embodiments may be applicable on all commercially available operating systems.

Application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, php. Python, ASP scripts, FORTRAN, COBOL, Perl, Java, ADA, .NET, and the like.

The I/O devices 570 may include input devices such as, for example but not limited to, a mouse, keyboard, scanner, microphone, camera, etc. Furthermore, the I/O devices 570 may also include output devices, for example but not limited to a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or intranet.

If the computer 500 is a PC, workstation, intelligent device or the like, the software in the memory 520 may further include a basic input output system (BIOS) (omitted for simplicity). The BIOS is a set of essential software routines that initialize and test hardware at startup, start the O/S 550, and support the transfer of data among the hardware devices. The BIOS is stored in some type of read-only-memory, such as ROM, PROM, EPROM, EEPROM or the like, so that the BIOS can be executed when the computer 500 is activated.

When the computer 500 is in operation, the processor 510 is configured to execute software stored within the memory 520, to communicate data to and from the memory 520, and to generally control operations of the computer 500 pursuant to the software. The application 560 and the O/S 550 are read, in whole or in part, by the processor 510, perhaps buffered within the processor 510, and then executed.

When the application 560 is implemented in software it should be noted that the application 560 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 560 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, optimized for embedded implementation, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

From the above description, it will be appreciated that embodiments may therefore be useful for monitoring of elderly, disabled or unwell individuals so to support independent living. Detected changes can be used both for real-time monitoring and alerts, as well as to detect when vital signs are/aren't reliable and/or when vital signs deviate from usual or expected patterns or trends.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand that various embodiments with various modifications are contemplated.

The invention claimed is:

1. A system for determining reliability of vital signs of a monitored subject, wherein the reliability is representative of a level of influence of activity on a vital sign, the system comprising:
    a signal interface for obtaining activity data relating to detected activity or posture of the monitored subject;
    a data acquisitioner for obtaining physiological data relating to one or more physical or physiological attributes of the monitored subject; wherein the one or more physical or physiological attributes of the monitored subject comprise at least one of: a height; a weight; an age; a gender; an existing disease; a relative size; an aerobic profile; an anaerobic power; a strength; an agility; a somatotype; a recovery ability; or a level of fitness; and
    a reliability processor for determining a measure of reliability of one or more vital signs of the monitored subject based on the activity data and the physiological data, comprising a duration of a recovery time required for the monitored subject to return to a resting state, wherein the reliability processor further measures an absolute difference of a current value of a vital sign from a resting state value of the vital sign.

2. The system of claim 1, further comprising:
    a sensor for detecting a value of the activity or posture of the monitored subject and generating a signal comprising activity data representative of the detected value, wherein the sensor comprises at least one of: an accelerometer; a gyroscope; a movement sensor; a weight sensor; a pressure sensor; or a timing device.

3. The system of claim 2, wherein the sensor is adapted to be coupled to the person or the object.

4. The system of claim 1, wherein the reliability processor further determines a resting state of the monitored subject based on the physiological data.

5. The system of claim 1, wherein the signal interface further obtains vital sign data relating to a detected value of a vital sign of the monitored subject,
    and wherein the system further comprises a prediction processor for determining a predicted value of the vital sign of the monitored subject at rest based on the vital sign data and the measure of reliability of one or more vital signs of the monitored subject.

6. The system of claim 1, wherein the reliability processor further:
    compares a value of the physiological data with one or more threshold values to obtain a comparison result;

generates a characterizing value based on the physiological data; and determines a measure of reliability of one or more vital signs of the monitored subject based on the comparison result and the characterizing value.

7. The system of claim 1, further comprising:

a historical data interface adapted to obtain historical data relating to previous activity or posture of the monitored subject, and wherein the reliability processor determines a measure of reliability of one or more vital signs of the monitored subject further based on the historical data.

8. The system of claim 1, wherein the reliability processor obtains a historical measure of reliability of one or more vital signs of the monitored subject, the historical measure of reliability having been previously determined for previously detected activity or posture of the monitored subject, and wherein the reliability processor determines a trend in the reliability of one or more vital signs of the monitored subject based on the determined measure of reliability and the historical measure of reliability.

9. The system of claim 1, wherein the activity data relating to detected activity or posture of the monitored subject comprises a value of at least one of: a velocity of movement of the subject; a measure of force applied by the subject to an object; a distance travelled by a part of the subject; a rate of acceleration of part of the subject; or a measure of posture of the subject.

10. A method implemented by a signal interface, a data acquisition unit and a processing system, for determining reliability of one or more vital signs of a monitored subject, wherein the reliability is representative of a level of influence of activity on a vital sign, the method comprising:

obtaining activity data relating to detected activity or posture of the monitored subject;

obtaining physiological data relating to one or more physical or physiological attributes of the monitored subject; wherein the one or more physical or physiological attributes of the monitored subject comprise at least one of: a height; a weight; an age; a gender; an existing disease; a relative size; an aerobic profile; an anaerobic power; a strength; an agility; a somatotype; a recovery ability; or a level of fitness; and determining a measure of reliability of one or more vital signs of the monitored subject based on the activity data and the physiological data, wherein the measure of reliability comprises a duration of a recovery time required for the monitored subject to return to a resting state; and determining an absolute difference of a current value of a vital sign from a resting state value of the vital sign.

11. The method implemented by a processing system, for monitoring vital signs of a subject, the method comprising:

obtaining vital signs data relating to one or more detected vital signs of the subject;

detecting a value of activity or posture of the monitored subject and to generate activity data representative of the detected value;

determining reliability of one or more vital signs of the monitored subject according to claim 10; and processing the vital signs data based on the determined reliability of one or more vital signs of the monitored subject, and preferably wherein processing the vital signs data comprises at least one of:

preventing an alarm from being activated;

postponing collection of further vital signs data relating to detected vital signs of the subject;

preventing the vital signs data relating to one or more detected vital signs of the subject from being provided to a warning system; and determining a value of a physical or physiological attribute of the subject based on the vital signs data and the determined reliability of one or more vital signs of the monitored subject.

12. A non-transitory computer program product comprising computer readable code storable on, or stored on, or downloadable from a communications network, which code when run on a computer implements the method of claim 10.

13. A system for monitoring vital signs of a subject, the system comprising:

an input interface for obtaining vital signs data relating to one or more detected vital signs of the subject;

a sensor arrangement for detecting a value of activity or posture of the monitored subject and to generate activity data representative of the detected value;

a system for determining a reliability of one or more vital signs of the monitored subject comprising:

a signal interface for obtaining activity data relating to detected activity or posture of the monitored subject;

a data acquisitioner for obtaining physiological data relating to one or more physical or physiological attributes of the monitored subject; wherein the one or more physical or physiological attributes of the monitored subject comprise at least one of: a height; a weight; an age; a gender; an existing disease; a relative size; an aerobic profile; an anaerobic power; a strength; an agility; a somatotype; a recovery ability; or a level of fitness; and a reliability processor for determining a measure of reliability of one or more vital signs of the monitored subject based on the activity data and the physiological data, comprising a duration of a recovery time required for the monitored subject to return to a resting state, wherein the reliability processor further measures an absolute difference of a current value of a vital sign from a resting state value of the vital sign; and a processor for processing the vital signs data based on the determined reliability of one or more vital signs of the monitored subject.

* * * * *